(12) United States Patent
Mehta et al.

(10) Patent No.: US 7,265,147 B2
(45) Date of Patent: Sep. 4, 2007

(54) 3,6-DISUBSTITUTED AZABICYCLO [3.1.0]HEXANE DERIVATIVES USEFUL AS MUSCARINIC RECEPTOR ANTAGONISTS

(75) Inventors: Anita Mehta, Plainfield, IL (US); Arundutt V. Silamkoti, Secunderabad (IN); Kirandeep Kaur, Haryana (IN); Jang Bahadur Gupta, Dusseldorf (DE)

(73) Assignee: Ranbaxy Laboratories Limited, Gurgaon, Haryana (IN)

( * ) Notice: Subject to any disclaimer, the term of this patent is extended or adjusted under 35 U.S.C. 154(b) by 50 days.

(21) Appl. No.: 10/523,208

(22) PCT Filed: Jul. 31, 2002

(86) PCT No.: PCT/IB02/02984

§ 371 (c)(1),
(2), (4) Date: Sep. 1, 2005

(87) PCT Pub. No.: WO2004/014853

PCT Pub. Date: Feb. 19, 2004

(65) Prior Publication Data

US 2006/0122253 A1    Jun. 8, 2006

(51) Int. Cl.
*A61K 31/403* (2006.01)
*C07D 209/52* (2006.01)
(52) U.S. Cl. .................. 514/412; 548/452
(58) Field of Classification Search .......... 548/452; 514/412

See application file for complete search history.

(56) References Cited

U.S. PATENT DOCUMENTS

| | | | | |
|---|---|---|---|---|
| 3,176,019 | A | 3/1965 | Campbell et al. | 260/293.4 |
| 4,183,857 | A | 1/1980 | Kollmeyer | 260/326.5 |
| 5,281,601 | A | 1/1994 | Cross et al. | 514/320 |
| 5,948,792 | A | 9/1999 | Tsuchiya et al. | 514/317 |
| 6,130,232 | A | 10/2000 | Mase et al. | 514/318 |
| 6,130,241 | A | 10/2000 | Schulz | 514/421 |
| 6,174,900 | B1 | 1/2001 | Okada et al. | 514/317 |
| 6,313,312 | B1 | 11/2001 | Banks et al. | 548/452 |

FOREIGN PATENT DOCUMENTS

| | | |
|---|---|---|
| EP | 0 325 571 | 7/1989 |
| EP | 0 388 054 | 9/1990 |
| EP | 0 801 067 | 10/1997 |
| GB | 940540 | 10/1963 |
| JP | 92921/1994 | 4/1994 |
| JP | 135958/1994 | 5/1994 |
| WO | WO91/09013 | 6/1991 |
| WO | WO93/16018 | 8/1993 |
| WO | WO93/16048 | 8/1993 |
| WO | WO96/33973 | 10/1996 |
| WO | WO97/45414 | 12/1997 |
| WO | WO98/05641 | 2/1998 |
| WO | WO98/29402 | 7/1998 |

OTHER PUBLICATIONS

Morissette et al. Advanced Drug Delivery Reviews 2004, 56, 275-300.*
Kubo et al., "Cloning, sequencing and expression of complementary DNA encoding the muscarinic acetylcholine receptor", *Nature*, 323(2):411-416 (1986).
Bonner et al., "Identification of a Family of Muscarinic Acetylcholine Receptor Genes", *Science*, 237:527-531 (1987).
Eglen et al., "Muscarinic receptor ligands and their theraputic potential", *Current Opinion in Chemical Biology*, 3:426-432 (1999).
Eglen et al., "Theraputic opportunities from muscarinic receptor research", *Trends in Pharmacological Sciences*, 22(8):409-414 (2001).
Felder et al., "Theraputic Opportunities for Muscarinic Receptors in the Central Nervous Systems", *Journal of Medicinal Chemistry*, 43(23):4333-4353 (2000).
Broadley and Kelly, "Muscarinic Receptor Agonists and Antagonists", *Molecules*, 6:142-193 (2001).
Birdsall et al., "Muscarinic receptors: it's a knockout", *Trends in Pharmacological Sciences*, 22(5):215-219 (2001).
de Groat and Yoshimura, "Pharmacology of the Lower Urinary Tract", *Annual Review of Pharmacology and Toxicology*, 41:691-721 (2001).
Steers, "The future direction of neuro-urology drug research", *Current Opinion in CPNS Investigational Drugs*, 2(3):268-282.
Chapple, "Muscarinic receptor antagonists in the treatment of overactive bladder", *Urology*, 55(Suppl. 5A):33-46 (2000).
Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).
Sagara et al, "Cyclohexylmethylpiperidinyltriphenylpropioamide: A Selective Muscarinic $M_3$ Antagonist Discriminating against the Other Receptor Subtypes", *Journal of Medicinal Chemistry*, 45(4):984-987 (2002).
Vogel's textbook, "Practical Organic Chemistry" 1046-1047 (5th Ed.).
Grover et al., "Chiral Mandelic Acid Template Provides a Highly Practical Solution for (S)-Oxybutynin Synthesis", *Journal of Organic Chemistry*, 65:6283-6287 (2000).
Cheng and Prusoff, "Relationship between the inhibition constant (*KI*) and the concentration of inhibitor which causes 50 per cent inhibition (*I50*) of an enzymatic reaction", *Biochemical Pharmacology*, 22:3099-3108 (1973).
Dobson and Raphael, "729. The synthesis of DL-baikiain", *Journal of the Chemical Society*, 3642-3647 (1958).

* cited by examiner

*Primary Examiner*—Kamal A. Saeed
*Assistant Examiner*—Jason M. Nolan
(74) *Attorney, Agent, or Firm*—Jayadeep R. Deshmukh, Esq.; George E. Heibel, Esq.

(57) ABSTRACT

This invention generally relates to the derivatives of 3,6 disubstituted azabicyclo[3.1.0]hexanes. The compounds of this invention are muscarinic receptor antagonists which are useful, inter-alia, for the treatment of various diseases of the respiratory, urinary and gastrointestinal systems mediated through muscarinic receptors. The invention also relates to a process for the preparation of compounds of the present invention, pharmaceutical compositions containing the compounds of the present invention and the methods for treating the diseases mediated through muscarinic receptors.

8 Claims, No Drawings

3,6-DISUBSTITUTED AZABICYCLO [3.1.0]HEXANE DERIVATIVES USEFUL AS MUSCARINIC RECEPTOR ANTAGONISTS

FIELD OF THE INVENTION

This invention generally relates to the derivatives of 3,6 disubstituted azabicyclo[3.1.0] hexanes.

The compounds of this invention are muscarinic receptor antagonists which are useful, inter-alia, for the treatment of various diseases of the respiratory, urinary and gastrointestinal systems mediated through muscarinic receptors.

The invention also relates to a process for the preparation of the compounds of the present invention, pharmaceutical compositions containing the compounds of the present invention and the methods for treating the diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cerebral cortex and autonomic ganglia, the $M_2$ subtype is present mainly in the heart where it mediates cholinergically induced bradycardia, and the $M_3$ subtype is located predominantly on smooth muscle and salivary glands (*Nature*, 1986; 323: 411; Science, 1987; 237: 527).

A review in Current opinions in Chemical Biology, 1999; 3: 426, as well as in *Trends in Pharmacological Sciences*, 2001; 22: 409 by Eglen et. al., describe the biological potentials of modulating muscarinic receptor subtypes by ligands in different disease conditions like Alzheimer's disease, pain, urinary disease condition, chronic obstructive pulmonary disease etc.

A review in J. Med. Chem., 2000; 43: 4333 by Christian C. Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in Molecules, 2001, 6: 142.

N. J. M. Birdsall et. al. in Trends in Pharmacological Sciences, 2001; 22: 215 have also summarized the recent developments on the role of different muscarinic receptor subtypes using different muscarinic receptor of knock out mice.

Muscarinic agonists such as muscarine and pilocarpine and antagonists such as atropine have been known for over a century, but little progress has been made in the discovery of receptor subtype-selective compounds making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options but most of them are not ideal anti-cholinergic bronchodilators due to lack of selectivity for muscarinic receptor sub-types. The existing compounds offer limited therapeutic benefit due to their lack of selectivity resulting in dose limiting side-effects such as thirst, nausea, mydriasis and those associated with the heart such as tachycardia mediated by the $M_2$ receptor.

Annual review of Pharmacological Toxicol., 2001; 41: 691, describes the pharmacology of the lower urinary tract infections. Although anti muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (W.D. Steers et. al. in Curr. Opin. Invest. Drugs, 2: 268, C.R. Chapple et. al. in Urology, 55: 33), Steers WD, Barrot DM, Wein AJ, 1996, Voiding dysfunction: diagnosis classification and management. In Adult and Pediatric Urology, ed. JY Gillenwatter, JT Grayhack, SS Howards, JW Duckett, pp 1220-1325, St. Louis, Mo.; Mosby. $3^{rd}$ edition.)

Despite these advances, there remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. U.S. Pat. Nos. 6,174,900, 6,130,232 and 5,948,792; WO 97/45414 are related to 1,4-disubstituted piperidine derivatives; WO 98/05641 describes fluorinated, 1,4-disubstituted piperidine derivatives; WO 93/16018 and W096/33973 are other close art references.

A report in J. Med. Chem., 2002; 44:984, describes cyclohexylmethyl piperidinyl triphenylpropioamide derivatives as selective $M_3$ antagonist discriminating against the other receptor subtypes.

SUMMARY OF THE INVENTION

The present invention provides 3,6-disubstituted azabicyclo[3.1.0]hexanes as muscarinic receptor antagonists which are useful as safe treatment of various diseases of the respiratory, urinary and gastrointestinal systems, and process for the synthesis of the compounds.

The invention also provides pharmaceutical compositions containing the compounds together with acceptable carriers, excipients or diluents which are useful for the treatment of various diseases of the respiratory, urinary and gastrointestinal systems.

The present invention also includes within its scope prodrugs of the compounds. In general, such prodrugs will be functionalized derivatives of these compounds which readily get converted in vivo into the defined compounds. Conventional procedures for the selection and preparation of suitable prodrugs are known to the artisan skilled in the art.

The invention also includes the enantiomers, diastereomers, polymorphs, pharmaceutically acceptable salts, pharmaceutically acceptable solvates, esters, N-oxides and metabolites of these compounds having the same type of activity.

The invention further includes pharmaceutical compositions comprising the compounds of the present invention, their enantiomers, diastereomers, prodrugs, polymorphs, pharmaceutically acceptable solvates, esters, N-oxides or metabolites, in combination with pharmaceutically acceptable carrier and optionally included excipients.

Other advantages of the invention will be set forth in the description which follows and in part will: be apparent from the description or may be learnt by the practice of the invention. The objects and the advantages of the invention may be realized and obtained by means of the mechanisms and combinations pointed out in the appended claims.

In accordance with one aspect of the present invention, there is provided a compound having the structure of Formula I:

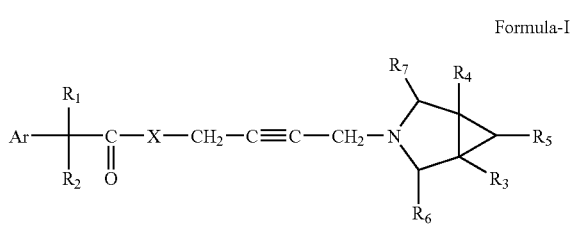

Formula-I and its pharmaceutically acceptable salts, pharmaceutically acceptable solvates, esters, enantiomers, diastereomers, N-oxides, polymorphs, prodrugs or metabolites, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), amino or lower alkyl ($C_1$-$C_4$) amino or N-lower alkyl ($C_1$-$C_4$) amino carbonyl;

$R_1$ represents a hydrogen, hydroxy, hydroxymethyl, amino, alkoxy, carbamoyl or halogen;

$R_2$ represents $C_1$-$C_4$ alkyl, $C_3$-$C_7$ cycloalkyl ring, a $C_3$-$C_7$ cycloalkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen (e.g. fluorine, chlorine, bromine, iodine), lower alkoxy ($C_1$-$C_4$), lower perhaloalkoxy ($C_1$-$C_4$), unsubstituted amino, lower alkyl ($C_1$-$C_4$) amino or N-lower alkyl ($C_1$-$C_4$) amino carbonyl;

X represents an oxygen, sulphur, nitrogen or no atom;

$R_3$, $R_4$, $R_5$, $R_6$ and $R_7$ independently represent, hydrogen, lower ($C_1$-$C_4$) alkyl, lower perhaloalkyl ($C_1$-$C_4$), cyano, hydroxyl, nitro, lower alkoxycarbonyl, halogen, lower ($C_1$-$C_4$) alkoxy, lower perhaloalkoxy ($C_1$-$C_4$), amino or lower alkyl ($C_1$-$C_4$) amino;

In accordance with a second aspect of the present invention, there is provided a method for treatment or prophylaxis of an animal or human suffering from a disease or disorder of the respiratory, urinary and gastrointestinal systems, wherein the disease or disorder is mediated through muscarinic receptors.

In accordance with a third aspect of the present invention, there is provided a method for treatment or prophylaxis of an animal or human suffering from a disease or disorder associated with muscarinic receptors, comprising administering to a patient in need thereof, an effective amount of muscarinic receptor antagonist compounds as described above.

In accordance with a fourth aspect of the present invention, there is provided a method for treatment or prophylaxis of an animal or human suffering from a disease or disorder of the respiratory system such as bronchial asthma, chronic obstructive pulmonary disorders (COPD), pulmonary fibrosis, etc.; urinary system which induce such urinary disorders as urinary incontinence, lower urinary tract symptoms (LUTS) etc.; and gastrointestinal system such as irritable bowel syndrome, obesity, diabetes and gastro intestinal hyperkinesis with compounds as described above, wherein the disease or disorder is associated with muscarinic receptors.

In accordance with a fifth aspect of the present invention, there are provided processes for preparing the compounds as described above.

The compounds of the present invention exhibit significant potency in terms of their activity, which was determined by in vitro receptor binding and functional assays and in vivo experiments using anaesthetized rabbit. The compounds that were found active in in vitro assay were tested in vivo. Some of the compounds of the present invention were found to be potent muscarinic receptor antagonists with high affinity towards $M_3$ receptors. Therefore, the present invention provides the pharmaceutical compositions for the possible treatment from the disease or disorders associated with muscarinic receptors. In addition the compounds of the present invention can be administered orally or parenterally.

DETAILED DESCRIPTION OF THE INVENTION

The compounds of the present invention may be prepared by techniques well known in the art and familiar to the average synthetic organic chemist. In addition, the compounds of the present invention may be prepared by the following inventive reaction sequence:

Scheme I

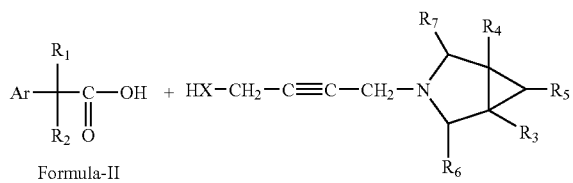

Formula-II        Formula-III

Condensing agent

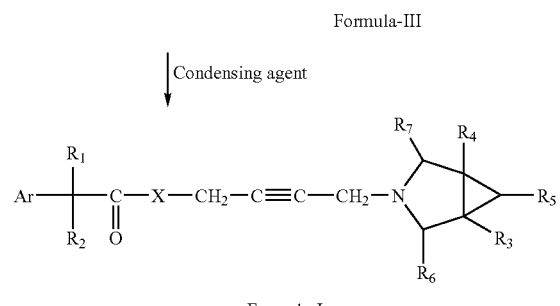

Formula-I

The compounds of Formula I of the present invention may be prepared by the reaction sequence as shown in Scheme I.

The preparation comprises condensing a compound of Formula II with the compound of Formula III wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), amino or lower alkyl ($C_1$-$C_4$) amino or N-lower alkyl ($C_1$-$C_4$) amino carbonyl;

$R_1$ represents a hydrogen, hydroxy, hydroxymethyl, amino, alkoxy, carbamoyl or halogen;

$R_2$ represents $C_1$-$C_4$ alkyl, $C_3$-$C_7$ cycloalkyl ring, a $C_3$-$C_7$ cycloalkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen (e.g. fluorine, chlorine, bromine, iodine), lower alkoxy ($C_1$-$C_4$), lower perhaloalkoxy ($C_1$-$C_4$), unsubstituted amino, lower alkyl ($C_1$-$C_4$) amino or N-lower alkyl ($C_1$-$C_4$) amino carbonyl;

X represents an oxygen, sulphur, nitrogen or no atom;

$R_3$, $R_4$, $R_5$, $R_6$ and $R_7$ independently represent, hydrogen, lower ($C_1$-$C_4$) alkyl, lower perhaloalkyl ($C_1$-$C_4$), cyano, hydroxyl, nitro, lower alkoxycarbonyl, halogen, lower ($C_1$-$C_4$) alkoxy, lower perhaloalkoxy ($C_1$-$C_4$), amino or lower alkyl ($C_1$-$C_4$) amino;

to give a compound of Formula I, wherein Ar, $R_1$, $R_2$, $R_3$, $R_4$, $R_5$, $R_6$, $R_7$ and X, are the same as defined earlier.

The condensation of the compound of Formula II with a compound of Formula III to give a compound of Formula I is carried out in the presence of a condensing agent which is selected from the group consisting of 1-(3-dimethylaminopropyl)-3-ethyl carbodiimide hydrochloride (EDC) and 1,8-diazabicyclo[5.4.0]undec-7-ene (DBU)

The condensation of the compound of Formula II with a compound of Formula III to give a compound of Formula I is carried out in a suitable solvent selected from the group consisting of N,N-dimethylformamide and dimethylsulphoxide. The reaction temperature and duration may be adjusted according to the desired needs.

Alternatively, the compounds of the present invention can be prepared by modified Mannich reaction of an acetylenic compound with an aldehyde and substituted azabicyclo [3.1.0] cyclohexane derivatives. The compounds of the invention can also be synthesised through ester-alcohol interchange involving 4-amino-2-butynyl alcohols and various alkyl esters or treatment of amino butynols with various acid chlorides or transesterification reactions.

Suitable salts of the compounds represented by the Formula I were prepared so as to solubilized the compound in aqueous medium for biological evaluations. Examples of such salts include pharmacologically acceptable salts such as inorganic acid salts (e.g. hydrochloride, hydrobromide, sulphate, nitrate and phosphorate), organic acid salts (e.g. acetate, tartarate, citrate, fumarate, maleate, tolounesulphonate and methanesulphonate). When carboxyl group is included in the Formula I as a substituent, it may be an alkali metal salt (e.g. sodium, potassium, calcium, magnesium, and the like). These salts may be prepared by the usual prior art techniques, such as treating the compound with an equivalent amount of inorganic or organic, acid or base in a suitable solvent.

Preferred compounds according to the invention and capable of being produced by Scheme I as shown in Table I include:

| Compound No. | Chemical Name |
|---|---|
| 1. | 4-[(1R, 5S)-1,5-dimethyl-3-azabicyclo [3.1.0]hex-3-yl]but-2-ynyl-2-hydroxy-2,2-diphenylacetate |
| 2. | 4-[(1R, 5S)-1,5-dimethyl-3-azabicyclo [3.1.0]hex-3-yl]but-2-ynyl-2-cyclohexyl-2-hydroxy phenylacetate. |
| 3. | 4-[(1R, 5S)-1,5-dimethyl-3-azabicyclo [3.1.0]hex-3-yl]but-2-ynyl-2-cyclopentyl-2-hydroxy phenyl acetate |
| 4. | 4-[(1R, 5S)-1-methyl-3-azabicyclo [3.1.0]-hex-3-yl] but-2-ynyl-2-hydroxy-2,2-diphenylacetate |
| 5. | 4-[(1R, 5S)-1-methyl-3-azabicyclo [3.1.0]-hex-3-yl]but-2-ynyl-2-cyclopentyl-2-hydroxy phenylacetate |
| 6. | 4-[(1R, 5S)-3-azabicyclo [3.1.0]-hex-3-yl]but-2-ynyl-2-hydroxy-2,2-diphenylacetate |
| 7. | 4-[(1R, 5S)-3-azabicyclo [3.1.0]-hex-3-yl]but-2-ynyl-2-cyclohexyl-2-hydroxy phenylacetate |
| 8. | 4-[(1R, 5S)-3-azabicyclo[3.1.0]-hex-3-yl]but-2-ynyl-2-cyclopentyl-2-hydroxy phenylacetate |
| 9. | N-{4-[(1R, 5S)-3-azabicyclo[3.1.0]-hex-3-yl]but-2-ynyl}-2-hydroxy-2-cyclohexyl-2-phenylacetamide |
| 10. | N-{4-[(1R, 5S)-3-azabicyclo[3.1.0]-hex-3-yl]but-2-ynyl}-2-hydroxy-2-cyclopentyl-2-phenylacetamide |
| 11. | N-{4-[(1R, 5S)-3-azabicyclo[3.1.0]-hex-3-yl]but-2-ynyl}-2-hydroxy-2,2-diphenylacetamide |
| 12. | N-{4-[(1R, 5S)-3-azabicyclo[3.1.0]hex-3-yl]but-2-ynyl}2-hydroxy-bis (4-fluorophenyl)acetamide |
| 13. | 4-[(1R,5S) -3-azabicyclo[3.1.0]hex-3-yl]-but-2-ynyl-2-hydroxy-bis-[4-fluorophenyl]acetate |
| 14. | 4-[(1R,5S) -3-azabicyclo[3.1.0]hex-3-yl]-but-2-ynyl-2-cyclopentyl-2-hydroxy-[4-methoxyphenyl]acetate |

| Compound No. | Chemical Name |
|---|---|
| 15. | 4-[(1R,5S)-3-azabicyclo[3.1.0]hex-3-yl]-but-2-ynyl-2-cyclopentyl-2-hydroxy(4-methyl phenyl)acetate |
| 16. | 4-[(1S,5R)-2-methyl-3-azabicyclo [3.1.0]hex-3-yl]but-2-ynyl-2-hydroxy-2,2-diphenyl acetate |
| 17. | 4-[(1S,5R)-2-methyl-3-azabicyclo[3.1.0]hex-3-yl]-but-2-ynyl-2-cyclopentyl-2-hydroxy phenylacetate |
| 18. | 4-[(1S,5R)-2-methyl-3-azabicyclo[3.1.0]hex-3-yl]-but-2-ynyl-2-cyclohexyl-2-hydroxy phenylacetate |
| 19. | 2R-(+),4-[(1R,5S)-3-azabicyclo[3.1.0]hex-3-yl]but-2-ynyl-2-cyclopentyl-2-hydroxy phenylacetate |
| 20. | 2S(−), 4-[(1R, 5S)-3-azabicyclo[3.1.0]hex-3-yl]but-2-ynyl-2-cyclopentyl-2-hydroxy phenyl acetate |
| 21. | 2R (+), 4[(1R, 5S)-3-azabicyclo[3.1.0]hex-3-yl]but-2-ynyl-2-cyclopentyl-2-hydroxy phenyl acetate hydrochloride. |

The illustrated list of the compounds is also given in Table-I.

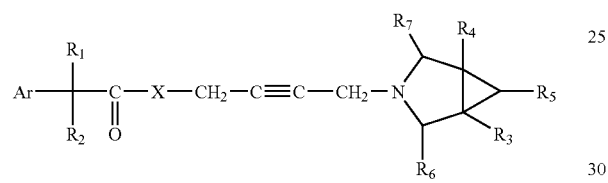

Formula-I

TABLE 1

| Comp No. | Ar | $R_1$ | $R_2$ | X | $R_3$ | $R_4$ | $R_5$ | $R_6$ | $R_7$ |
|---|---|---|---|---|---|---|---|---|---|
| 1 | phenyl | OH | phenyl | O | $CH_3$ | $CH_3$ | H | H | H |
| 2 | phenyl | OH | cyclohexyl | O | $CH_3$ | $CH_3$ | H | H | H |
| 3 | phenyl | OH | cyclopentyl | O | $CH_3$ | $CH_3$ | H | H | H |
| 4 | phenyl | OH | phenyl | O | $CH_3$ | H | H | H | H |
| 5 | phenyl | OH | cyclopentyl | O | $CH_3$ | H | H | H | H |
| 6 | phenyl | OH | phenyl | O | H | H | H | H | H |
| 7 | phenyl | OH | cyclohexyl | O | H | H | H | H | H |

TABLE 1-continued
| Comp No. | Ar | R₁ | R₂ | X | R₃ | R₄ | R₅ | R₆ | R₇ |
|---|---|---|---|---|---|---|---|---|---|
| 8 | 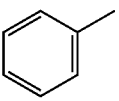 | OH | 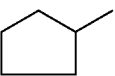 | O | H | H | H | H | H |
| 9 | 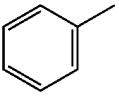 | OH | 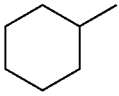 | NH | H | H | H | H | H |
| 10 | 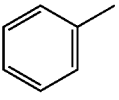 | OH | 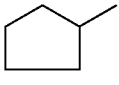 | NH | H | H | H | H | H |
| 11 | 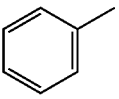 | OH | 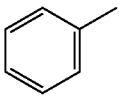 | NH | H | H | H | H | H |
| 12 | 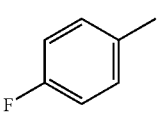 | OH | 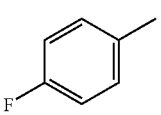 | NH | H | H | H | H | H |
| 13 | 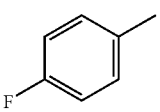 | OH | 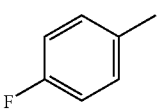 | O | H | H | H | H | H |
| 14 | 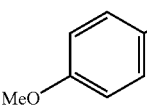 | OH | 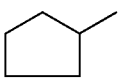 | O | H | H | H | H | H |
| 15 | 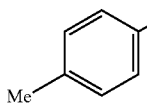 | OH | 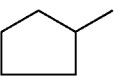 | O | H | H | H | H | H |
| 16 | 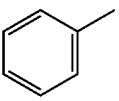 | OH | 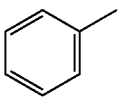 | O | H | H | H | CH₃ | H |
| 17 | 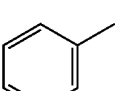 | OH | 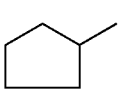 | O | H | H | H | CH₃ | H |
| 18 | 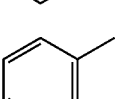 | OH | 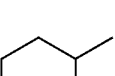 | O | H | H | H | CH₃ | H |
| 19 | 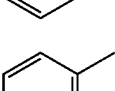 | OH | 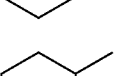 | O | H | H | H | H | H |
| 20 | 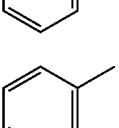 | OH |  | O | H | H | H | H | H |

TABLE 1-continued

| Comp No. | Ar | R₁ | R₂ | X | R₃ | R₄ | R₅ | R₆ | R₇ |
|---|---|---|---|---|---|---|---|---|---|
| 21 | phenyl | OH | cyclopentyl | O | H | H | H | H | H |

Because of their valuable pharmacological properties, the compounds of the present invention may be administered to an animal for treatment orally, or by parenteral route. The pharmaceutical compositions of the present invention are preferably produced and administered in dosage units, each unit containing a certain amount of at least one compound of the invention and/or at least one physiologically acceptable salt addition thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The examples mentioned below demonstrate the general synthetic procedure as well as the specific preparation of the preferred compound. The examples are provided to illustrate the details of the invention and should not be construed to limit the scope of the present invention.

Experimental Details

IR spectra were recorded as nujol mulls or a thin neat film on a Perkin Elmer Paragon instrument. Nuclear Magnetic Resonance (NMR) data (H, C) were recorded on a Varian XL-300 MHz instrument using tetramethylsilane as an internal standard.

EXAMPLE 1

Preparation of 4-[(1R, 5S)-1,5-dimethyl-3-azabicyclo[3.1.0]hex-3-yl]but-2-ynyl-2-hydroxy-2,2-diphenylacetate (Compound No. 1)

Step a: Preparation of 2-hydroxy-2,2-diphenyl acetic acid:
Synthesized as per reported procedure in Vogel's textbook of practical organic chemistry page 1046 (5th Ed).

Step b: Preparation of 1,5-dimethyl-3-azabicyclo[3.1.0] hexane hydrochloride:
Synthesized as per reported procedure of U.S. Pat. No. 4,183,857, using methyl methacrylate and ethyl 2-chloropropionate instead of ethyl acrylate and ethyl chloroacetate.

Step c: Preparation of 1-chloro-4-hydroxy-2-butyne:
Synthesized as per reported procedure of Journal of American Chemical Society, 1955; 77:165.

Step d: Preparation of 4-(1,5-dimethyl-3-azabicyclo [3.1.0]hex-3-yl)-2-butynol
To a stirring solution of 1,5-dimethyl-3-azabicyclo[3.1.0] hexane hydrochloride (0.3 gm, 2 mmol) in chloroform (50 ml), 1-chloro-4-hydroxy-2-butyne (0.11 gm, 1 mmol), followed by triethylamine (0.3 gm, 3 mmol) were added. The reaction mixture was refluxed for 3 hours and then allowed to cool to room temperature. The solvents were evaporated in vacuo. The residual oil was purified by column chromatography using silicagel (100-200 mesh), eluting the compound with 50-50 ethyl acetate-hexane mixture.

$^1$H-NMR (CDCl$_3$) δ—values: 4.28 (s, 2H), 3.37 (s, 2H), 2.91-2.88 (d, 2H), 2.38-2.35 (d, 1H), 1.09 (s, 6H), 0.94 (m, 1H), 0.012 (m, 1H).

Step e: Preparation of 4-[(1R, 5S)-1,5-dimethyl-3-azabicyclo[3.1.0]hex-3-yl]but-2-ynyl-2-hydroxy-2,2-diphenylacetate:
To a solution of 4-(1,5-dimethyl-3-azabicyclo[3.1.0]hex-3-yl)-2-butynol (1 mmol, 0.18 gm) in DMF (5 ml) was added 2-hydroxy-2,2-diphenyl acetic acid (1 mmol, 0.225 gm) and cooled to 0° C. The reaction mixture was treated with hydroxy benzotriazole (1 mmol, 0.135 gm) followed by N-methyl morpholine (2 mmol, 0.202 gm) and stirred at 0° C. for 0.5 hrs. EDC (1-[3-(dimethylamino)propyl]-3-ethyl carbodiimide hydrochloride (1 mmol, 0.192 gm) was added and the reaction mixture was sturred at 0° C. for 1 hr. and at room temperature for two days. Then, the reaction mixture was poured into cold water and extracted with ethyl acetate. The combined organic layers were washed with water and dried over sodium sulphate. The crude compound obtained after removing the solvent was purified by column chromatography (silicagel 100-200 mesh), eluting the compound with 20-80 ethylacetate-hexane mixture.

$^1$H-NMR (CDCl$_3$) δ—values: 7.47-7.26 (m, arom, 10H), 4.85 (s, 2H), 4.13 (b, 1H), 3.36 (s, 2H), 2.86-2.83 (d, 2H), 2.34-2.32 (d, 2H), 1.08 (s, 6H), 0.93-0.92 (d, 1H), 0.001 (d,1H).

IR (DCM): 1738 cm$^{-1}$

EXAMPLE 2

Preparation of 4-[(1R, 5S)-1,5-dimethyl-3-azabicyclo[3.1.0]hex-3-yl]but-2-ynyl-2-cyclohexyl-2-hydroxy phenylacetate (Compound No. 2)

Step a: Preparation of 2-hydroxy-2-cyclohexyl phenyl acetic acid:
This was prepared following the procedure as described in J. Amer. Chem. Soc. 1953; 75:2654.

Step b: Preparation of 4-[(1R,5S)-1,5-dimethyl-3-azabicyclo[3.1.0]hex-3-yl]but-2-ynyl-2-cyclohexyl-2-hydroxy phenylacetate:
To a solution of 4-(1,5-dimethyl-3-azabicyclo[3.1.0]hex-3-yl)-2-butynol (1 mmol, 0.18 gm) in DMF (5 ml) was added 2-hydroxy-2-cyclohexyl phenylacetic acid (1 mmol, 0.234 gin) and cooled to 0° C. The reaction mixture was treated with hydroxy benzotriazole (1 mmol, 0.135 g) followed by N-methyl morpholine (2 mmol, 0.202 gm) and stirred at 0° C. for 0.5 hours. EDC (1 mmol, 0.192 gm) was then added. The reaction mixture after being stirred at 0° C. for 1 hr. was later stirred at room temperature for 2 days. The reaction mixture was poured into cold water and extracted with ethylacetate. The organic layer was dried over sodium sulphate. The crude compound obtained after removing the solvent was purified by column chromatography (silica gel 100-200 mesh), eluting the compound With 20-80 ethylacetate-hexane mixture.

¹H-NMR (CDCl₃) δ—values: 7.66-7.17 (m, arom, 5H), 4.86-4.68 (dd, 2H), 3.6 (s, 1H), 3.39-3.35 (d, 2H), 2.86-2.82 (m, 2H), 2.34-2.30 (m, 3H), 1.65-0.92 (m, 17H), 0.013(d, 1H).
IR (DCM): 1731 cm⁻¹

EXAMPLE 3

Preparation of 4-[(1R, 5S)-1,5-dimethyl-3-azabicyclo[3.1.0]hex-3-yl]but-2-ynyl-2-cyclopentyl-2-hydroxy phenyl acetate (Compound No. 3)

Step a: Preparation of 2-hydroxy-2-cyclopentyl phenyl acetic acid:
This was prepared following the procedure as described in J. Amer. Chem. Soc. 1953; 75:2654.

Step b: Preparation of 4-[(1R, 5S)-1,5-dimethyl-3-azabicyclo[3.1.0]hex-3-yl]but-2-ynyl-2-cyclopentyl-2-hydroxy phenyl acetate:
To a solution of 4-(1,5-dimethyl-3-azabicyclo[3.1.0]hex-3-yl)-2-butynol (1 mmol, 0.18 gm) in DMF (5 ml) was added 2-hydroxy-2-cyclopentyl-2-phenyl acetic acid (1 mmol, 0.22 gm) and cooled to 0° C. The reaction mixture was treated with hydroxy benzotriazole (1 mmol, 0.135 g) followed by N-methyl morpholine (2 mmol, 0.202 gm) and stirred at 0° C. for 0-5 hours. EDC (1 mmol, 0.192 gm) was then added and the reaction mixture after being stirred at 0° C. for 1 hr. was stirred at room temperature for 2 days. The reaction mixture was poured into water and extracted with ethylacetate. The organic layer was dried over sodium sulphate. The crude compound obtained after evaporation of solvent was purified by column chromatography (silicagel 100-200 mesh), eluting the compound with 20-80 ethyl acetate-hexane mixture.
¹H-NMR (CDCl₃) δ—values: 7.67-7.24 (m, arom, 5H), 4.86-4.66 (dd, 2H), 3.66 (s, 1H), 3.36 (s, 2H), 2.92-2.83 (m, 3H), 2.36-2.32 (m, 2H), 1.68-0.92 (m, 15H), 0.0103(d,1H).
IR (DCM): 1731 cm⁻¹

EXAMPLE 4

Preparation of 4-[(1R, 5S)-1-methyl-3-azabicyclo[3.1.0]hex-3-yl]but-2-ynyl-2-hydroxy-2,2-diphenylacetate (Compound No. 4)

Step a: Preparation of 1-methyl-3-azabicyclo[3.1.0]hexane hydrochloride:
Synthesized as per reported procedure of U.S. Pat. No. 4,183,857, using ethyl 2-chloropropionate instead of ethyl chloroacetate.

Step b: Preparation of 4-(1-methyl-3-azabicyclo[3.1.0]hex-3-yl)-2-butynol:
The compound of Step-b was prepared by following the procedure described in Step-d of Example-1, using 1-methyl-3-azabicyclo[3.1.0]hexane hydrochloride instead of 1,5-dimethyl-3-azabicyclo[3.1.0]hexane hydrochloride.
¹HNMR (CDCl₃) δ—values: 4.28 (d, 2H), 3.53-3.48 (d, 2H), 2.9-2.87 (m, 2H), 2.64-2.6 (m, 1H), 2.43-2.4 (m, 1H), 2.125 (b, 1H), 1.22 (s, 3H), 1.06 (m, 1H), 0.87 (m, 1H), 0.3-0.26 (m, 1H)

Step c: Preparation of 4-[(1R, 5S)-1-methyl-3-azabicyclo[3.1.0]-hex-3-yl]but-2-ynyl-2-hydroxy-2,2-diphenylacetate:
The compound of Step-c was prepared by following the procedure described in Step-e of Example-1, using 4-(1-methyl-3-azabicyclo[3.1.0]hex-3-yl)-2-butynol instead of 4-(1,5-dimethyl-3-azabicyclo[3.1.0]hex-3-yl)-2-butynol.

¹H-NMR (CDCl₃) δ—values: 7.46-7.17 (m, arom, 10H), 4.93 (b, 1H), 4.84 (s, 2H), 3.37 (m, 2H), 2.83-2.77 (m, 2H), 2.59-2.55 (m, 1H), 2.39-2.36 (m, 1H), 1.2 (s, 3H), 1.03 (m, 1H), 0.85 (m, 1H), 0.29 (m, 1H).
IR (DCM): 1740 cm⁻¹

EXAMPLE 5

Preparation of 4-[(1R, 5S)-1-methyl-3-azabicyclo[3.1.0]-hex-3-yl]but-2-ynyl-2-cyclopentyl-2-hydroxyphenylacetate (Compound No. 5)

The title compound was prepared by following the procedure described in Step-b of Example-3, using 4-(1-methyl-3-azabicyclo[3.1.0]hex-3-yl)-2-butynol instead of 4-(1,5-dimethyl-3-azabicyclo[3.1.0]hex-3-yl)-2-butynol.
¹H-NMR (CDCl₃) δ—values: 7.67-7.19 (m, arom, 5H), 4.85-4.67 (dd, 2H), 3.87 (b, 1H), 3.39 (s, 2H), 2.93 (m, 1H), 2.84 (m, 2H), 2.59 (m, 1H), 2.39 (m, 1H), 1.68-0.83 (m, 13H), 0.28 (m,1H).
IR (DCM): 1732 cm⁻¹

EXAMPLE 6

Preparation of 4-[(1R, 5S)-3-azabicyclo[3.1.0]-hex-3-yl]but-2-ynyl-2-hydroxy-2,2-diphenylacetate (Compound No. 6)

Step a: Preparation of 3-azabicyclo[3.1.0]hexane hydrochloride:
Synthesized as per reported procedure of U.S. Pat. No. 4,183,857.

Step b: Preparation of 4-(3-azabicyclo[3.1.0]hex-3-yl)-2-butynol:
The compound of Step-b was prepared by following the procedure described in Step-d of Example-1, using 3-azabicyclo[3.1.0]hexane hydrochloride instead of 1,5-dimethyl-3-azabicyclo[3.1.0]hexane hydrochloride.
¹H-NMR (CDCl₃) δ—values: 4.3 (s, 2H), 3.43 (s, 2H), 2.96-2.93 (d, 2H), 2.63-2.61 (m, 2H), 1.39-1.25 (m, 2H), 0.71-0.67 (m,1H), 0.42-0.36 (m, 1H).

Step c: Preparation of 4-[(1R, 5S)-3-azabicyclo[3.1.0]-hex-3-yl]but-2-ynyl-2-hydroxy-2,2-diphenylacetate:
The compound of Step-c was prepared by following the procedure described in Step-e of Example-1, using 4-(3-azabicyclo[3.1.0]hex-3-yl)-2-butynol instead of 4-(1,5-dimethyl-3-azabicyclo[3.1.0]hex-3-yl)-2-butynol.
¹H-NMR (CDCl₃) δ—values: 7.46-7.26 (m, 10H), 4.85 (s, 2H), 3.46 (s, 2H), 2.95-2.92 (m, 2H), 2.65-2.62 (m, 2H), 2.04 (m, 2H), 1.40-1.38 (m, 2H), 0.76-0.75 (m, 1H), 0.47-0.40 (m, 1H).
IR (DCM): 1740 cm⁻¹

EXAMPLE 7

Preparation of 4-[(1R, 5S)-3-azabicyclo[3.1.0]-hex-3-yl]but-2-ynyl-2-cyclohexyl-2-hydroxy phenylacetate (Compound No. 7)

The title compound was prepared by following the procedure described in Step-b of Example-2, using 4-(3-azabicyclo[3.1.0]hex-3-yl)-2-butynol instead of 4-(1,5-dimethyl-3-azabicyclo[3.1.0]hex-3-yl)-2-butynol.
¹H-NMR (CDCl₃) δ—values: 7.66-7.26 (m, 5H), 4.81-4.72 (dd, 2H), 3.6 (s, 1H), 3.39-3.38 (d, 2H), 2.86-2.82 (m, 2H), 2.55-2.52 (m, 2H), 1.37-1.11 (m, 13H), 0.67-0.66 (m, 1H), 0.44-0.42 (m, 1H).

IR (DCM): 1731 cm$^{-1}$

EXAMPLE 8

Preparation of 4-[(1R, 5S)-3-azabicyclo[3.1.0]-hex-3-yl]but-2-ynyl-2-cyclopentyl-2-hydroxy phenylacetate (Compound No. 8)

The title compound was prepared by following the procedure described in Step-b of Example-3, using 4-(3-azabicyclo[3.1.0]hex-3-yl)-2-butynol instead of 4-(1,5-dimethyl-3-azabicyclo[3.1.0]hex-3-yl)-2-butynol.

$^1$H-NMR (CDCl$_3$) δ—values: 7.66-7.28 (m, 5H), 4.85-4.67 (dd, 2H), 3.65 (s, 1H), 3.39 (s, 2H), 2.92-2.83 (m, 2H), 2.55-2.52 (m, 2H), 1.55-1.25 (m, 11H), 0.67-0.654 (m,1H), 0.38-0.36 (m, 1H).

IR (DCM): 1731 cm$^{-1}$

EXAMPLE 9

Preparation of N-{4-[(1R, 5S)-3-azabicyclo[3.1.0]-hex-3-yl]but-2-ynyl}-2-hydroxy-2-cyclohexyl-2-phenylacetamide (Compound No. 9)

Step a: Preparation of 1-(3-azabicyclo[3.1.0]hex-3-yl)-4-phthalimido but-2-yne:

To a solution of 3-azabicyclo[3.1.0]hexane hydrochloride (0.12 gm, 1 mmol) in chloroform (50 ml), was added triethyl amine (0.3 gm, 3 mmol) followed by 1-chloro-4-phthalimido but-2-yne (Journal of Chemical Society, 1958; 3643, 0.235 gm, 1 mmol). The reaction mixture was refluxed for 12 hours and then allowed to attain room temperature. The reaction mixture was concentrated in vacuo to afford an oily residue which was purified by column chromatography (silica gel 100-200 mesh) eluting the compound with 20-80 ethyl acetate-hexane mixture (mp 108-109° C.).

$^1$H-NMR (CDCl$_3$) δ—values: 7.89-7.72 (m, 4H), 4.43 (s, 2H), 3.34 (s, 2H), 2.86-2.84 (m, 2H), 2.57-2.54 (m, 2H), 1.34-1.32 (m, 2H), 0.66-0.62 (m, 1H), 0.37-0.31 (m, 1H).

IR (DCM): 1706 cm$^{-1}$

Step-b: Preparation of 1-amino-4-(3-azabicyclo[3.1.0]hex-3-yl)-but-2-yne:

An alcoholic solution of the compound of Example 9, Step a (0.28 gm, 1 mmol) was refluxed with hydrazine hydrate (0.05 gm, 1 mmol) for 3 hours. The gelatinous precipitate was decomposed by heating with excess of aqueous hydrochloric acid for half an hour. Phthalyl hydrazide was separated by hot filtration, and the filtrate was cooled. It was concentrated and filtered again. The filtrate was made alkaline with aqueous sodium hydroxide (20%) and extracted with ethyl acetate. The organic layer was washed with water, dried over sodium sulphate and concentrated in vacuo to afford the title compound as an oily residue.

$^1$H-NMR (CDCl$_3$): δ—values: 3.44-3.38 (dd, 4H), 2.95-2.92 (m, 2H), 2.61-2.59 (m, 2H), 1.82-1.36 (m, 2H), 0.73-0.70 (m, 1H), 0.42-0.35 (m, 1H).

Step c: Preparation of N-{4-[(1R, 5S)-3-azabicyclo[3.1.0]-hex-3-yl]but-2-ynyl}-2-hydroxy-2-cyclohexyl-2-phenylacetamide:

The title compound was prepared by following the procedure described in Step-b of Example-2, using 1-amino-4-(3-azabicyclo[3.1.0]hex-3-yl)-but-2-yne instead of 4-(1,5-dimethyl-3-azabicyclo[3.1.0]hex-3-yl)-2-butynol.

$^1$H-NMR (CDCl$_3$) δ—values: 7.62-7.23 (m, 5H), 6.83 (b, 1H), 4.07-3.93 (m, 2H), 3.35 (s, 2H), 2.91-2.88 (m, 2H), 2.57-2.54 (m, 2H), 1.67-1.16 (m, 13H), 0.68-0.67 (m,1H), 0.39-0.38 (m, 1H).

IR (DCM): 1661 cm$^{-1}$

EXAMPLE 10

Preparation of N-{4-[(1R, 5S)-3-azabicyclo[3.1.0]-hex-3-yl]but-2-ynyl}-2-hydroxy-2-cyclopentyl-2-phenylacetamide (Compound No. 10)

The title compound was prepared by following the procedure described in Step-b of Example-3, using 1-amino-4-(3-azabicyclo[3.1.0]hex-3-yl)-but-2-yne instead of 4-(1,5-dimethyl-3-azabicyclo[3.1.0]hex-3-yl)-2-butynol.

$^1$H-NMR (CDCl$_3$) δ—values: 7.61-7.25 (m, 5H), 6.60 (b, 1H), 4.0-3.95 (m, 2H), 3.32 (s, 2H), 2.87-2.84 (m, 2H), 2.53-2.5 (m, 2H), 1.63-1.24 (m, 11H), 0.67-0.65 (m,1H), 0.37-0.35 (m, 1H).

IR (DCM): 1660 cm$^{-1}$

EXAMPLE 11

Preparation of N-{4-[(1R, 5S)-3-azabicyclo[3.1.0]-hex-3-yl]but-2-ynyl}-2-hydroxy-2,2-diphenylacetamide (Compound No. 11)

The title compound was prepared by following the procedure described in Step-e of Example-1, using 1-amino-4-(3-azabicyclo[3.1.0]hex-3-yl)-but-2-yne instead of 4-(1,5-dimethyl-3-azabicyclo[3.1.0]hex-3-yl)-2-butynol.

$^1$H-NMR (CDCl$_3$) δ—values: 7.45-7.22 (m, 10H), 6.75 (b, 1H), 4.10 (s, 2H), 3.42 (s, 2H), 2.99-2.94 (m, 2H), 2.69-2.66 (m, 2H), 1.28-1.25 (m, 2H), 0.49-0.46 (m,1H), 0.45-0.42 (m, 1H).

IR (DCM): 1659 cm$^{-1}$

EXAMPLE 12

Preparation of N-{4-[(1R,5S)-3-azabicyclo[3.1.0]-hex-3-yl]-but-2-ynyl}2-hydroxy-bis(4-florophenyl) acetamide (Compound No. 12)

Step a: Preparation of 2-hydroxy-2,2-di(4-fluorophenyl) acetic acid:

Synthesized as per reported procedure in Vogel's textbook of practical organic chemistry page 1046 (5$^{th}$ Ed), using 4-fluoro benzaldehyde instead of benzaldehyde.

Step b: To a solution of 1-amino-4-(3-azabicyclo[3.1.0]hex-3-yl)-but-2-yne (1 mmol, 0.15 gm) in DMF (5 ml) was added 2-hydroxy-2,2-di-(4-fluorophenyl)acetic acid (1 mmol, 0.236 gm) and cooled to 0° C. The reaction mixture was treated with hydroxy benzotriazole (1 mmol, 0.135 g) followed by N-methyl morpholine (2 mmol, 0.202 gm) and stirred at 0° C. for 0.5 hrs. EDC (1-[3-(dimethylamino)propyl]-3-ethyl carbodiimide hydrochloride (1 mmol. 0.192 gm) was then added. The reaction mixture after stirring at 0° C. for 1 hr. was later stirred at room temperature for two days. Then the reaction mixture was poured into cold water and extracted with ethyl acetate. The combined organic layers were washed with water and dried over sodium sulphate. The crude compound obtained after removing the solvent was purified by column chromatography (silicagel 100-200 mesh), eluting the compound with 20-80 ethylacetate-hexane mixture.

¹H-NMR (CDCl₃) δ—values: 7.43-7.39 (m, 4H), 7.06-7.0 (m, 4H), 6.9 (b, 1H), 4.12 (s, 2H) 3.44 (s,2H), 3.04-3.01 (m, 2H), 2.70-2.68 (m, 2H), 1.43 (m, 2H), 0.49 (m,1H), 0.47 (m, 1H).

IR (DCM): 1665 cm$^{-1}$

EXAMPLE 13

Preparation of 4-[(1R,5S)-3-azabicyclo[3.1.0]hex-3-yl]-but-2-ynyl-2-hydroxy-bis-[4-fluorophenyl]acetate (Compound No. 13)

The title compound was prepared by following the procedure described in Step-b of Example-12, using 4-(3-azabicyclo[3.1.0]hex-3-yl)-2-butynol instead of 1-amino-4-(3-azabicyclo[3.1.0]hex-3-yl)-but-2-yne.

¹H-NMR (CDCl₃) δ—values: 7.43-7.38 (m, 4H), 7.06-7.0 (m, 4H), 4.86 (s, 2H), 4.1 (s, 1H), 3.5 (s, 2H), 3.03-3.0 (m, 2H), 2.70-2.68 (m, 2H), 1.45-1.42 (m, 2H), 0.84-0.3 (m, 1H), 0.50-0.48 (m, 1H).

IR (DCM): 1741 cm$^{-1}$

EXAMPLE 14

Preparation of 4-[(1R,5S)-3-azabicyclo[3.1.0]hex-3-yl]but-2-ynyl-2-cyclopentyl-2-hydroxy-[4-methoxyphenyl]acetate (Compound No. 14)

Step a: Preparation of 2-cyclopentyl-2-hydroxy-2-(4-methoxyphenyl)acetic acid. This compound was synthesised as per reported procedure in Syn. Comm., 1981; 11 (12):943.

Step b: The title compound was prepared by following the procedure described in Step-b of Example-3, using 2-cyclopentyl-2-hydroxy-2-(4-methoxyphenyl)acetic acid instead of 2-cyclopentyl-2-hydroxy-2-phenyl acetic acid and 4-(3-azabicyclo[3.1.0]hex-3-yl)-2-butynol instead of 4-(1,5-dimethyl-3-azabicyclo[3.1.0]hex-3-yl)-2-butynol.

¹H-NMR (CDCl₃) δ—values: 7.57-7.54 (m, 2H), 6.88-6.85 (m, 2H), 4.84-4.68 (m, 2H), 3.80 (s, 3H), 3.62 (s, 1H), 3.46 (s, 2H), 2.96-2.65 (m, 4H), 1.66-1.26 (m, 11H), 0.77 (m, 1H), 0.45 (m, 1H).

IR (DCM): 1731 cm$^{-1}$

EXAMPLE 15

Preparation of 4-[(1R,5S)-3-azabicyclo[3.1.0]hex-3-yl]-but-2-ynyl-2-cyclopentyl-2-hydroxy(4-methyl phenyl)acetate (Compound No. 15)

Step a: Preparation of 2-cyclopentyl-2-hydroxy-2-(4-methylphenyl)acetic acid. This compound was synthesised as per reported procedure in Syn. Comm., 1981; 11 (12):943.

Step b: The title compound was prepared by following the procedure described in Step-b of Example-3, using 2-cyclopentyl-2-hydroxy-2-(4-methylphenyl)acetic acid instead of 2-cyclopentyl-2-hydroxy-2-phenylacetic acid and 4-(3-azabicyclo[3.1.0]hex-3-yl)-2-butynol instead of 4-(1,5-dimethyl-3-azabicyclo[3.1.0]hex-3-yl)-2-butynol.

¹H-NMR (CDCl₃) δ—values: 7.48-7.45 (m, 2H), 7.09-7.06 (m, 2H), 4.77-4.59 (dd, 2H), 3.56 (s, 1H), 3.32 (s, 2H), 2.79-2.76 (m, 2H), 2.49-2.46 (m, 2H), 2.27 (s, 3H), 1.61-1.18 (m, 11H), 0.59 (m, 1H), 0.32 (m, 1H).

IR (DCM): 1730 cm$^{-1}$

EXAMPLE 16

Preparation of 4-[(1S,5R)-2-methyl-3-azabicyclo[3.1.0]hex-3-yl]but-2-ynyl-2-hydroxy-2,2-diphenyl acetate (Compound No. 16)

Step a: Preparation of 3-benzyl-4-hydroxy-4-methyl-3-azabicyclo[3.1.0]hexan-2-one:3-benzyl-3-azabicyclo[3.1.0]hexane-2,4-dione (Prepared as per U.S. Pat. No. 4,183,857, 1.9 gm, 9.5 mmol) was dissolved in 100 ml of tetrahydrofuran and cooled to −78° C. Methyllithium (10.5 ml of a 0.98M solution in ether, 10.2 mmol) was added dropwise. Saturated aqueous ammonium chloride was added to the cold reaction mixture. The mixture was then extracted with ethyl acetate. The combined organic layers were dried over sodium sulphate, filtered and concentrated in vacuo to provide the title compound.

¹H-NMR (CDCl₃) δ—values: 7.28-7.17 (m, 5H), 4.63-4.58 (d, 1H), 4.24-4.18 (d, 1H), 3.01 (s, 1H), 2.16-2.03 (m, 2H), 1.25 (s,3H), 0.80 (m, 1H), 0.65 (m, 1H).

IR (KBr): 1655 cm$^{-1}$

Step b: Preparation of 3-benzyl-2-methyl-3-azabicyclo[3.1.0]hexane:

A solution of the compound obtained at step a (1.5 gm, 7 mmol) in tetrahydrofuran (100 ml) was treated with lithium aluminum hydride (0.8 gm, 21 mmol) and heated to reflux for 16 hrs. The cold reaction mixture was then treated with saturated aqueous ammonium chloride, precipitated solids were filtered off and the filtrate concentrated to afford the title compound as an oily residue.

¹H-NMR (CDCl₃) δ—values: 7.31-7.19 (m, 5H), 3.9-3.87 (d, 1H), 3.18-3.14 (d, 1H), 2.89-2.86 (d, 1H), 2.69 (m, 1H), 2.33-2.29 (m, 1H), 1.35-1.21 (m, 2H), 1.14-1.12 (d, 3H), 0.73-0.71 (m, 1H), 0.19-0.18 (m, 1H).

IR (DCM): 1637 cm$^{-1}$

Step c: Preparation of 2-methyl-3-azabicyclo[3.1.0]hexane hydrochloride:

The compound of step b, (1.0 gm) was dissolved in methanol (50 ml) and treated with palladium oil charcoal (10% by weight, 0.2 gm) and subjected to parr hydrogenation at 45 psi for 6 hrs. The reaction mixture was then filtered and the filtrate was acidified with concentrated hydrochloric acid. The solvents were evaporated to afford the title compound.

¹H-NMR (CDCl₃) δ—values: 3.91 (b, 1H), 3.49-3.44 (m, 2H), 1.66-1.63 (m, 2), 1.53-1.51 (d, 3H), 1.02-0.97 (m, 1H), 0.73-0.65 (m, 1H).

Step d: Preparation of 4-(2-methyl-3-azabicyclo[3.1.0]hex-3-yl)-2-butynol.

The compound of Step-d was prepared by following the procedure described in Step-d of Example-1, using 2-methyl-3-azabicyclo[3.1.0]hexane hydrochloride instead of 1,5-dimethyl-3-azabicyclo[3.1.0]hexane hydrochloride.

¹H-NMR (CDCl₃) δ—values: 4.28 (s, 2H), 3.50-3.31 (dd, 2H), 2.98-2.95 (d, 1H), 2.88-2.77 (m, 2H), 1.38-1.25 (m, 2H), 1.06-1.04 (d, 3H), 0.65-0.63 (m, 1H), 0.26-0.23 (m, 1H).

Step e: Preparation of 4-[(1S,5R)-2-methyl-3-azabicyclo[3.1.0]hex-3-yl]but-2-ynyl-2-hydroxy-2,2-diphenyl acetate:

The compound of Step-e was prepared by following the procedure described in Step-e of Example-1, using 4-(2-methyl-3-azabicyclo[3.1.0]hex-3-yl)-2-butynol instead of 4-(1,5-dimethyl-3-azabicyclo[3.1.0]hex-3-yl)-2-butynol.

¹H-NMR (CDCl₃) δ—values: 7.47-7.26 (m, 10H), 4.85 (s, 2H), 4.12 (s, 1H), 3.41-3.31 (dd, 2H), 2.91-2.71 (m, 3H), 1.36-1.25 (m, 2H), 1.03-1.01 (d, 3H), 0.63-0.62 (m, 1H), 0.25-0.24 (m, 1H).
IR (DCM): 1739 cm⁻¹

EXAMPLE 17

Preparation of 4-[(1S,5R)-2-methyl-3-azabicyclo [3.1.0]hex-3-yl]-but-2-ynyl-2-cyclopentyl-2-hydroxyphenylacetate (Compound No. 17)

The compound was prepared by following the procedure described in Step-b of Example-3, using 4-(2-methyl-3-azabicyclo[3.1.0]hex-3-yl)-2-butynol instead of 4-(1,5-dimethyl-3-azabicyclo[3.1.0]hex-3-yl)-2-butynol.
¹-NMR (CDCl₃) δ—Values: 7.67-7.26 (m, arom, 5H), 4.85-4.67 (dd, 2H), 3.66 (s, 1H), 3.46-3.36 (dd, 2H), 2.92-2.71 (m, 4H), 1.58-1.25 (m, 10H), 1.03-1.01(d, 3H), 0.62-0.61 (m, 1H), 0.25-0.23 (m, 1H).
IR (DCM): 1731 cm⁻¹

EXAMPLE 18

Preparation of 4-[(1S,5R)-2-methyl-3-azabicyclo [3.1.0]hex-3-yl]-but-2-ynyl-2-cyclohexyl-2-hydroxyphenylacetate (Compound No. 18)

The compound was prepared by following the procedure described in Step-b of Example-2, using 4-(2-methyl-3-azabicyclo[3.1.0]hex-3-yl)-2-butynol instead of 4-(1,5-dimethyl-3-azabicyclo[3.1.0]hex-3-yl)-2-butynol.
¹H-NMR (CDCl₃) δ—values: 7.66-7.26 (m, arom, 5H), 4.86-4.68 (dd, 2H), 3.62 (s, 1H), 3.46-3.36 (dd, 2H), 2.90-2.26 (m, 4H), 1.64-1.10 (m, 13H), 1.03-1.02(d, 3H), 0.7 (m, 1H), 0.3 (m, 1H).
IR (DCM): 1730 cm⁻¹

EXAMPLE 19

Preparation of 2R-(+),4-[(1R,5S)-3-azabicyclo [3.1.0]hex-3-yl]but-2ynyl-2-cyclopentyl-2-hydroxy phenyl acetate (Compound No. 19)

Step a: Preparation of (2R)(−)-2-hydroxy-2-cyclopentyl-2-phenyl acetic acid:
Synthesized as per reported procedure of Paul T. Grover, et. al. J. Org. Chem. 2000; 65:6283.
Step b: The title compound was synthesised following the procedure as in step-b of Example-3, using the (2R)(−)-2-hydroxy-2-cyclopentyl-2-phenyl acetic acid instead of the Corresponding racemic acid and 4-(3-azabicyclo[3.1.0]hex-3-yl)-2-butynol instead of 4-(1,5-dimethyl-3-azabicyclo [3.1.0]hex-3-yl)-2-butynol.
¹H-NMR (CDCl₃) δ—values: 7.67-7.26 (m, 5H), 4.85-4.70 (dd, 2H), 3.63 (s, 1H), 3.51 (s, 2H), 2.98-2.90 (m, 4H), 1.68-1.33 (m, 11H), 0.8 (m, 1H), 0.45 (m, 1H).
IR (DCM): 1731 cm⁻¹

EXAMPLE 20

Preparation of 2S(−),4-[(1R,5S)-3-azabicyclo[3.1.0] hex-3-yl]but-2-ynyl-2-cyclopentyl-2-hydroxyphenyl acetate (Compound No. 20)

Step a: Preparation of (2S)(+)2-hydroxy-2-cyclopentyl-2-phenyl acetic acid:
Synthesized as per reported procedure of Paul T. Grover, et. al. 3. Org. Chem. 2000; 65:6283.
Step b: The title compound was synthesized following the procedure as in Step-b of Example 3: using the (2S)(+)2-hydroxy-2-cyclopentyl-2-phenyl acetic acid instead of the corresponding racemic acid and 4-(3-azabicyclo[3.1.0]hex-3-yl)-2-butynol instead of 4-(1,5-dimethyl-3-azabicyclo [3.1.0]hex-3-yl)-2-butynol.
¹H-NMR (CDCl₃) δ—values: 7.66-7.26 (m, 5H), 4.80-4.76 (dd, 2H), 3.63 (s, 1H), 3.52 (s, 2H), 3.01-2.90 (m, 4H), 1.67-1.33 (m, 11H), 0.5 (m, 1H), 0.3 (m, 1H).
IR (DCM): 1731 cm⁻¹

EXAMPLE 21

Preparation of 2R(+),4-[(1R,5S)-3-azabicyclo[3.1.0] hex-3-yl]but-2-ynyl-2-cyclopentyl-2-hydroxyphenyl acetate hydrochloride (Compound No. 21)

To a solution of compound of Example 19 (0.2 gm) in diethyl ether (5 ml) at room temperature was added a ethereal hydrochloric acid (5 ml, 20%). The reaction mixture was stirred for half an hour and then filtered. The residue obtained was dried to afford the title compound (mp 152-155° C.).
1H-NMR (DMSO-d₆) δ—values: 7.57-7.26 (m, 5H), 5.85 (s, 1H), 4.84 (s, 2H), 4.11 (s, 2H), 3.19-2.82 (m, 4H), 1.71-1.16 (m, 11H), 0.6 (m, 1H), 0.5 (m, 1H).
IR (KBr): 1749 cm⁻¹

Pharmacological Testing Results

Radioligand Binding Assays:

The affinity of test compounds for $M_2$ and $M_3$ muscarinic receptor subtypes was determined by [³H]-N-methylscopolamine binding studies using rat heart and submandibular gland respectively as described by Moriya et al., (Life Sci, 1999,64(25):2351) with minor modifications.

Membrane preparation: Submandibular glands and heart were isolated and placed in ice cold homogenising buffer (HEPES 20 mM, 10 mM EDTA, pH 7.4) immediately after sacrfice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, 5 mM, pH 7.4) and were stored at −70° C. until the time of assay.

Ligand binding assay: The compounds were dissolved and diluted in DMSO. The membrane homogenates (150-250 μg protein) were incubated in 250 μl of assay buffer (HEPES 20 mM, pH 7.4) at 24-25° C. for 3 hours. Non-specific binding was determined in the presence of 1 μM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The $IC_{50}$ & Kd were estimated by using the non-linear curve fitting program using G Pad Prism software. The value of inhibition constant Ki was calculated from competitive binding studies by using Cheng & Prusoff equation (*Biochem Pharmacol*, 1973;22: 309), Ki=$IC_{50}$/(1+

L/Kd), where L is the concentration of [³H]NMS used in the particular experiment.

Functional Experiments Using Isolated Rat Bladder:

Methodology:

Animals were euthanized by overdose of urethane and whole bladder was isolated and removed rapidly and placed in ice cold Tyrode buffer with the following composition (mMol/L) NaCl 137; KCl 2.7; CaCl$_2$ 1.8; MgCl$_2$ 0.1; NaHCO$_3$ 11.9; NaH$_2$PO$_4$ 0.4; Glucose 5.55 and continuously gassed with 95% O$_2$ and 5% CO$_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period the stabilization of the tissue contractile response was assessed with 1 μMol/L of Carbachol consecutively for 2-3 times. Subsequently a cumulative concentration response curve to carbachol ($10^{-9}$ mol/L to $3 \times 10^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB=−log [(molar concentration of antagonist/(dose ratio−1))]

where, dose ratio=$ED50$ in the presence of antagonist/$ED50$ in the absence of antagonist.

In Vivo Experiments Using Anaesthetised Rabbit

Methodology

Male rabbits were anaesthetised with urethane 1.5 g/kg intravenously. Trachea was cannulated to maintain the patency of airway. Femoral vein and femoral arteries of both sides were cannulated for the administration of vehicle or drug substances for the measurement of BP and administration of carbachol intra-arterially respectively.

Polyethylene tubing was introduced into the bladder through the urethra and tied at the neck of the bladder. The other end of the catheter was connected to the Grass polygraph through a Statham pressure transducer. The bladder was filled with warm (37° C.) saline. Both the ureters were ligated and cut proximally to drain the urine coming from kidneys. A stabilization period of 30-60 was allowed for stabilization of parameters from surgical procedures.

Salivary response was assessed by measuring the weight of a preweighted cotton gauze kept for 2 minutes in the buccal cavity immediately after the carbachol challenge.

At the end of stabilization period 2 control responses to carbachol (1.5 μg/kg intra-arterial) on bladder pressure and salivation were obtained and this response was considered as 100%. Subsequently, the effect of increasing dose of NCE (ranging from 3 μg/kg to 1 mg/kg) or vehicle (i.v., 15 min before carbachol challenge) was examined.

The change in bladder pressure and salivation were expressed as % change from pretreatment control averages. The $ID_{50}$ values for salivation and bladder pressure inhibition were calculated using Graph Pad Prism software, by fitting the values at dose into non-linear regression curve. Oxybutynin and Tolterodine were used as standards for comparison.

The bladder selectivity to salivation was calculated by using following formula and expressed as fold of selectivity of oxybutinin in the same model.

$$\frac{ID_{50} \text{ Salivary response}}{ID_{50} \text{ Bladder pressure}}$$

The results are listed in Tables II.

In-Vitro Tests

TABLE II

| | Receptor Binding Assay Ki (nM) | | | Functional |
|---|---|---|---|---|
| | $M_2$ | $M_3$ | Selectivity ($M_2/M_3$) | Assay $pK_B$ |
| Compound No. 1 | 508 | 528 | 0.96 | |
| Compound No. 2 | 337 | 282 | 1.19 | |
| Compound No. 3 | 355 | 347 | 1.02 | |
| Compound No. 4 | 827 | 358 | 2.31 | |
| Compound No. 5 | 438 | 191 | 2.29 | |
| Compound No. 6 | 31 | 14 | 2.21 | 8.1 |
| Compound No. 7 | 72 | 35 | 2.05 | 7.64 |
| Compound No. 8 | 65 | 37 | 1.75 | 8.12 |
| Compound No. 9 | 3582 | 2605 | 1.37 | 6.82 |
| Compound No. 10 | 425 | 330 | 1.28 | 7.01 |
| Compound No. 11 | 639 | 291 | 2.19 | |
| Compound No. 12 | 736 | 366 | 2.01 | |
| Compound No. 13 | 40 | 39 | 1.025 | |
| Compound No. 14 | 1926 | 964 | 1.99 | |
| Compound No. 15 | 28 | 16 | 1.75 | 7.22 |
| Compound No. 16 | 209 | 48 | 4.354 | |
| Compound No. 17 | 142 | 39 | 3.641 | |
| Compound No. 18 | 185 | 24 | 7.708 | |
| Compound No. 19 | 22 | 6.0 | 3.66 | |
| Compound No. 20 | 224 | 102 | 2.19 | |
| Compound No. 22 | 26.4 | 12.5 | 2.11 | 8.31 |
| Tolterodine | 5.3 | 4.0 | 1.32 | 2.0 |
| Oxybutynin | 6.97 | 0.95 | 7.34 | 2.0 |
| Atropine | 0.93 | 0.2 | 4.65 | |

While the present invention has been described in terms of its specific embodiments, certain modifications and equivalents will be apparent to those skilled in the art and are intended to be included within the scope of the present invention.

What is claimed is:

1. A compound having the structure of Formula I:

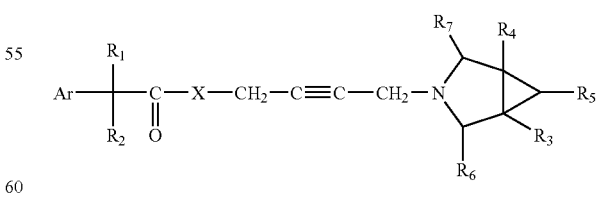

Formula-I and its pharmaceutical acceptable salts, pharmaceutically acceptable enantiomers, diastereomers, N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one two three substituents independently selected from lower alkyl ($C_1$-$C_4$), lower perhalo alkyl ($C_1$-$C_4$), cyano, hydroxy, nitro, lower alkoxy ($C_1$-$C_4$), lower perhaloalkoxy ($C_1$-$C_4$), amino or lower alkyl ($C_1$-$C_4$) amino or N-lower alkyl ($C_1$-$C_4$) amino carbonyl;

$R_1$ represents a hydrogen, hydroxy, hydroxy methyl, amino, alkoxy, carbamoyl or halogen;

$R_2$ represents $C_1$-$C_4$ alkyl, $C_3$-$C_7$ cycloalkyl ring, a $C_3$-$C_7$ cycloalkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhaloalkyl ($C_1$-$C_4$), cyano, hydroxy, nitro, lower alkoxy carbonyl, halogen, lower alkoxy carbonyl halogen, lower alkoxy ($C_1$-$C_4$), lower per haloalkoxy ($C_1$-$C_4$), unsubstituted amino, lower alkylamino ($C_1$-$C_4$) or N-lower alkyl ($C_1$-$C_4$) aminocarbonyl;

X represents an oxygen, sulphur, nitrogen or no atom; and $R_3$, $R_4$, $R_5$, $R_6$ and $R_7$ independently represent, a hydrogen, lower alkyl ($C_1$-$C_4$), lower perhaloalkyl ($C_1$-$C_4$), cyano, hydroxyl, nitro, lower alkoxy carbonyl, halogen, lower alkoxy ($C_1$-$C_4$), lower perhaloalkoxy ($C_1$-$C_4$), amino or lower alkyl ($C_1$-$C_4$) amino.

2. A compound selected from the group consisting of:
4-[(1R, 5S)-1,5-dimethyl-3-azabicyclo[3.1.0]hex-3-yl]but-2-ynyl-2-hydroxy-2,2-diphenylacetate (Compound No. 1),
4-[(1R, 5S)-1,5-dimethyl-3-azabicyclo[3.1.0]hex-3-yl]but-2-ynyl-2-cyclohexyl-2-hydroxy phenylacetate (Compound No. 2),
4-[(1R, 5S)-1,5-dimethyl-3-azabicyclo[3.1.0]hex-3-yl]but-2-ynyl-2-cyclopentyl-2-hydroxy phenyl acetate (Compound No. 3),
4-[(1R, 5S)-1-methyl-3-azabicyclo[3.1.0]-hex-3-yl]but-2-ynyl-2-hydroxy-2,2-diphenylacetate (Compound No. 4),
4-[(1R, 5S)-1-methyl-3-azabicyclo[3.1.0]hex-3-yl]but-2-ynyl-2-cyclopentyl-2-hydroxy phenylacetate (Compound No. 5),
4-[(1R, 5S)-3-azabicyclo[3.1.0]-hex-3-yl]but-2-ynyl-2-hydroxy-2,2-diphenylacetate (Compound No. 6),
4-[(1R, 5S)-3-azabicyclo[3.1.0]-hex-3-yl]but-2-ynyl-2-cyclohexyl-2-hydroxy phenylacetate (Compound No. 7),
4-[(1R, 5S)-3-azabicyclo[3.1.0]-hex-3-yl]but-2-ynyl-2-cyclopentyl-2-hydroxy phenylacetate (Compound No. 8),
N-{4-[(1R, 5S)-3-azabicyclo[3.1.0]-hex-3-yl]but-2-ynyl}-2-hydroxy-2-cyclohexyl-2-phenylacetamide (Compound No. 9),
N-{4-[(1R, 5S)-3-azabicyclo[3.1.0]-hex-3-yl]but-2-ynyl}-2-hydroxy-2-cyclopentyl-2-phenylacetamide (Compound No. 10),
N-{4-[(1R, 5S)-3-azabicyclo[3.1.0]-hex-3-yl]but-2-ynyl}-2-hydroxy-2,2-diphenylacetamide (Compound No. 11),
N-{4-[(1R, 5S)-3-azabicyclo[3.1.0]-hex-3-yl]-but-2-ynyl}2-hydroxy-bis(4-fluorophenyl)acetamide (Compound No. 12),
4-[(1R,5S)-3-azabicyclo[3.1.0]hex-3-yl]-but-2-ynyl-2-hydroxy-bis-[4-fluorophenyl]acetate (Compound No. 13),
4-[(1R,5S)-3-azabicyclo[3.1.0]hex-3-yl]-but-2-ynyl-2-cyclopentyl-2-hydroxy-[4-methoxyphenyl]acetate (Compound No. 14),
4-[(1R,5S)-3-azabicyclo[3.1.0]hex-3-yl]-but-2-ynyl-2-cyclopentyl-2-hydroxy(4-methylphenyl)acetate (Compound No. 15),
4-[(1S,5R)-2-methyl-3-azabicyclo[3.1.0]hex-3-yl]butyt-2-ynyl-2-hydroxy-2,2-diphenyl acetate (Compound No. 16),
4-[(1S,5R)-2-methyl-3-azabicyclo(3.1.0)hex-3-yl]-but-2-ynyl-2-cyclopentyl-2-hydroxyphenylacetate (Compound No. 17),
4-[(1S,5R)-2-methyl-3-azabicyclo[3.1.0]hex-3-yl]-but-2-ynyl-2-cyclohexyl-2-hydroxy phenylacetate (Compound No. 18),
2-R-(+),4-[(1R,5S)-3-azabicyclo[3.1.0]hex-3-yl]but-2-ynyl-2-cyclopentyl-2-hydroxy phenylacetate (Compound No. 19),
2S(-),4-[(1R, 5S)-3-azabicyclo[3.1.0]hex-3-yl]but-2-ynyl-2-cyclopentyl-2-hydroxy phenyl acetate (Compound No. 20), and
2R(+),4-[(1R, 5S)-3-azabicyclo[3.1.0]hex-3-yl]but-2-ynyl-2-cyclopentyl-2-hydroxy phenylacetate hydrochloride (Compound No. 21).

3. A pharmaceutical composition comprising a therapeutically effective amount of a compound as defined in claim 1 or 2 together with pharmaceutically acceptable carriers, excipients or diluents.

4. A method for treatment of an animal or human suffering from a disease or disorder of the respiratory, urinary and gastrointestinal systems, wherein the disease or disorder is mediated through muscarinic receptors, wherein the disease or disorder is urinary incontinence, lower urinary tract symptoms (LUTS) chronic obstructive pulmonary disorders (COPD), irratable bowel symdrome or gastro intestinal hyperkinesis, comprising administering to said animal or human, a therapeutically effective amount of a compound having the structure of Formula I,

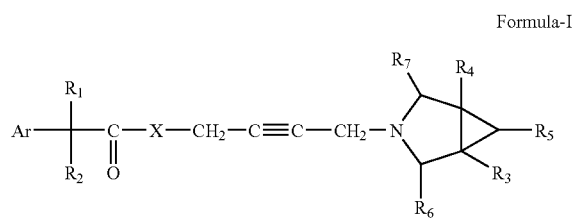

Formula-I or its pharmaceutical acceptale salts, pharmaceutically acceptable enantiomers, diastereomers, N-oxides, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one two three substituents independently selected from lower alkyl ($C_1$-$C_4$), lower perhalo alkyl ($C_1$-$C_4$), cyano, hydroxy, nitro, lower alkoxy ($C_1$-$C_4$), lower perhaloalkoxy ($C_1$-$C_4$), amino or lower alkyl ($C_1$-$C_4$) amino or N-lower alkyl ($C_1$-$C_4$) amino carbonyl;

$R_1$ represents a hydrogen, hydroxy, hydroxy methyl, amino, alkoxy, carbamoyl or halogen;

$R_2$ represents $C_1$-$C_4$ alkyl, $C_3$-$C_7$ cycloalkyl ring, a $C_3$-$C_7$ cycloalkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhaloalkyl ($C_1$-$C_4$), cyano, hydroxy, nitro, lower alkoxy carbonyl, halogen, lower alkoxy carbonyl halogen, lower alkoxy ($C_1$-$C_4$), lower per haloalkoxy ($C_1$-$C_4$), unsubstituted amino, lower alkylamino ($C_1$-$C_4$) or N-lower alkyl ($C_1$-$C_4$) aminocarbonyl;

X represents an oxygen, sulphur, nitrogen or no atom; and $R_3$, $R_4$, $R_5$, $R_6$ and $R_7$ independently represent, hydrogen, lower alkyl ($C_1$-$C_4$), lower perhaloalkyl ($C_1$-$C_4$), cyano, hydroxyl, nitro, lower alkoxy carbonyl, halogen, lower alkoxy ($C_1$-$C_4$), lower perhaloalkoxy ($C_1$-$C_4$), amino or lower alkyl ($C_1$-$C_4$) amino.

5. The method for treatment of an animal or human suffering from a disease or disorder of the respiratory, urinary and gastrointestinal systems, wherein the disease or disorder is mediated through muscarinic receptors, wherein the disease or disorder is urinary incontinence, lower uninary tract symptoms (LUTS), chronic obstructive pulmonary dosorders (COPD), irritable bowel syndrome or gastro intestinal hyperkinesis, comprising administering to said animal or human, a therapeutically effective amount of the pharmaceutical composition according to claim 3.

6. A process of preparing a compound of Formula I,

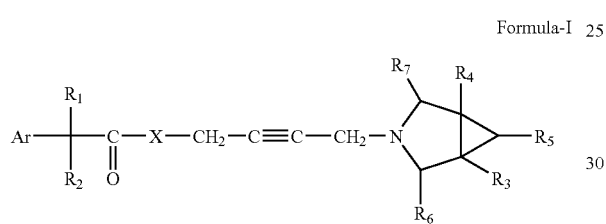

Formula-I or its pharmaceutically acceptable salts, pharmaceutically acceptable enantiomers, diastereomers, N-oxides, wherein:

Ar represents an aryl or a heteroaryl ring having 1-2 hetero atoms selected from the group consisting of oxygen, sulphur and nitrogen atoms, the aryl or heteroaryl rings may be unsubstituted or substituted by one two three substituents independently selected from lower alkyl ($C_1$-$C_4$), lower perhalo alkyl ($C_1$-$C_4$), cyano, hydroxy, nitro, lower alkoxy ($C_1$-$C_4$), lower perhaloalkoxy ($C_1$-$C_4$), amino or lower alkyl ($C_1$-$C_4$) amino or N-lower alkyl ($C_1$-$C_4$) amino carbonyl;

$R_1$ represents a hydrogen, hydroxy, hydroxy methyl, amino, alkoxy, carbamoyl or halogen;

$R_2$ represents $C_1$-$C_4$ alkyl, $C_3$-$C_7$ cycloalkyl ring, a $C_3$-$C_7$ cycloalkenyl ring, an aryl or a heteroaryl ring having 1 to 2 hetero atoms selected from a group consisting of oxygen, sulphur and nitrogen atoms; the aryl or a heteroaryl ring may be unsubstituted or substituted by one to three substituents independently selected from lower alkyl ($C_1$-$C_4$), lower perhaloalkyl ($C_1$-$C_4$), cyano, hydroxy, nitro, lower alkoxy carbonyl, halogen, lower alkoxy carbonyl halogen, lower alkoxy ($C_1$-$C_4$), lower per haloalkoxy ($C_1$-$C_4$), unsubstituted amino, lower alkylamino ($C_1$-$C_4$) or N-lower alkyl ($C_1$-$C_4$) aminocarbonyl;

X represents an oxygen, sulphur, nitrogen or no atom; and $R_3$, $R_4$, $R_5$, $R_6$ and $R_7$ independently represent, hydrogen, lower alkyl ($C_1$-$C_4$), lower perhaloalkyl ($C_1$-$C_4$), cyano, hydroxyl, nitro, lower alkoxy carbonyl, halogen, lower alkoxy ($C_1$-$C_4$), lower perhaloalkoxy ($C_1$-$C_4$), amino or lower alkyl ($C_1$-$C_4$) amino, said process comprising:

condensing a compound of Formula II with a compound of Formula III

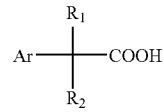

Formula-II

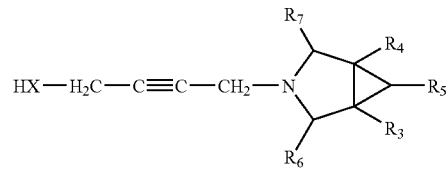

Formula III in the presence of a condensing agent to give a compound of Formula I.

7. The process according to claim 6 wherein the condensing agent is selected from the group consisting of 1-(3-dimethyl amino propyl)-3-ethyl carbodiimide hydrochloride (EDC) and 1,8-diazabicyclo[5.4.0]undec-7-ene (DBU).

8. The process according to claim 6 wherein the solvent is selected from the group consisting of dimethylformamide (DMF), acetonitrile, and toluene.

* * * * *